(12) United States Patent
Borgmann et al.

(10) Patent No.: US 7,494,276 B2
(45) Date of Patent: Feb. 24, 2009

(54) METHOD AND SYSTEM FOR THE PLANNING OF IMAGING PARAMETERS

(75) Inventors: Ludger Borgmann, Hamburg (DE); Clemens Krucken, Hamburg (DE)

(73) Assignee: Koninklijke Philips Electronics N.V., Eindhoven (NL)

( * ) Notice: Subject to any disclaimer, the term of this patent is extended or adjusted under 35 U.S.C. 154(b) by 0 days.

(21) Appl. No.: 11/576,530

(22) PCT Filed: Sep. 29, 2005

(86) PCT No.: PCT/IB2005/053216

§ 371 (c)(1), (2), (4) Date: Apr. 3, 2007

(87) PCT Pub. No.: WO2006/038165

PCT Pub. Date: Apr. 13, 2006

(65) Prior Publication Data

US 2007/0242806 A1    Oct. 18, 2007

(30) Foreign Application Priority Data

Oct. 5, 2004    (EP)    .................................. 04300654

(51) Int. Cl.
*G01D 18/00* (2006.01)
*H05G 1/28* (2006.01)

(52) U.S. Cl. ........................ 378/207; 378/162; 378/165

(58) Field of Classification Search ................. 378/98.5, 378/98.7, 63, 64, 147, 162, 163, 205–207
See application file for complete search history.

(56) References Cited

U.S. PATENT DOCUMENTS

| | | | |
|---|---|---|---|
| 5,251,635 A | 10/1993 | Doumoulin et al. | |
| 5,539,798 A * | 7/1996 | Asahina et al. | ............ 378/98.5 |
| 5,617,462 A | 4/1997 | Spratt | |
| 6,447,163 B1 * | 9/2002 | Bani-Hashemi et al. | ...... 378/205 |
| 7,198,404 B2 * | 4/2007 | Navab et al. | ................ 378/206 |
| 2002/0012450 A1 | 1/2002 | Osamutsujii | |
| 2003/0165216 A1 | 9/2003 | Walker et al. | |

FOREIGN PATENT DOCUMENTS

| | | |
|---|---|---|
| DE | 10327293 A1 | 1/2005 |
| FR | 2634094 A | 1/1990 |
| FR | 2825610 A | 12/2002 |
| JP | 63294839 A2 | 1/1988 |
| JP | 06339541 | 12/1994 |

* cited by examiner

*Primary Examiner*—Irakli Kiknadze

(57) ABSTRACT

A method and an assistance system (20) plan geometrical imaging parameters like the active dose-measuring-field (29) and/or the opening of a collimator (12) of an X-ray device (10). An optical image (27) of a patient (1) on a table (2) is generated by a camera (21) and transferred to a computer (25). The computer (25) then overlays said optical image (27) of the patient (1) with a graphical representation of the geometrical imaging parameters, for example with a drawing of the available and/or activated dose-measuring-fields (28, 29). The user may thus control and interactively select values of the imaging parameters on the overlay image.

18 Claims, 1 Drawing Sheet

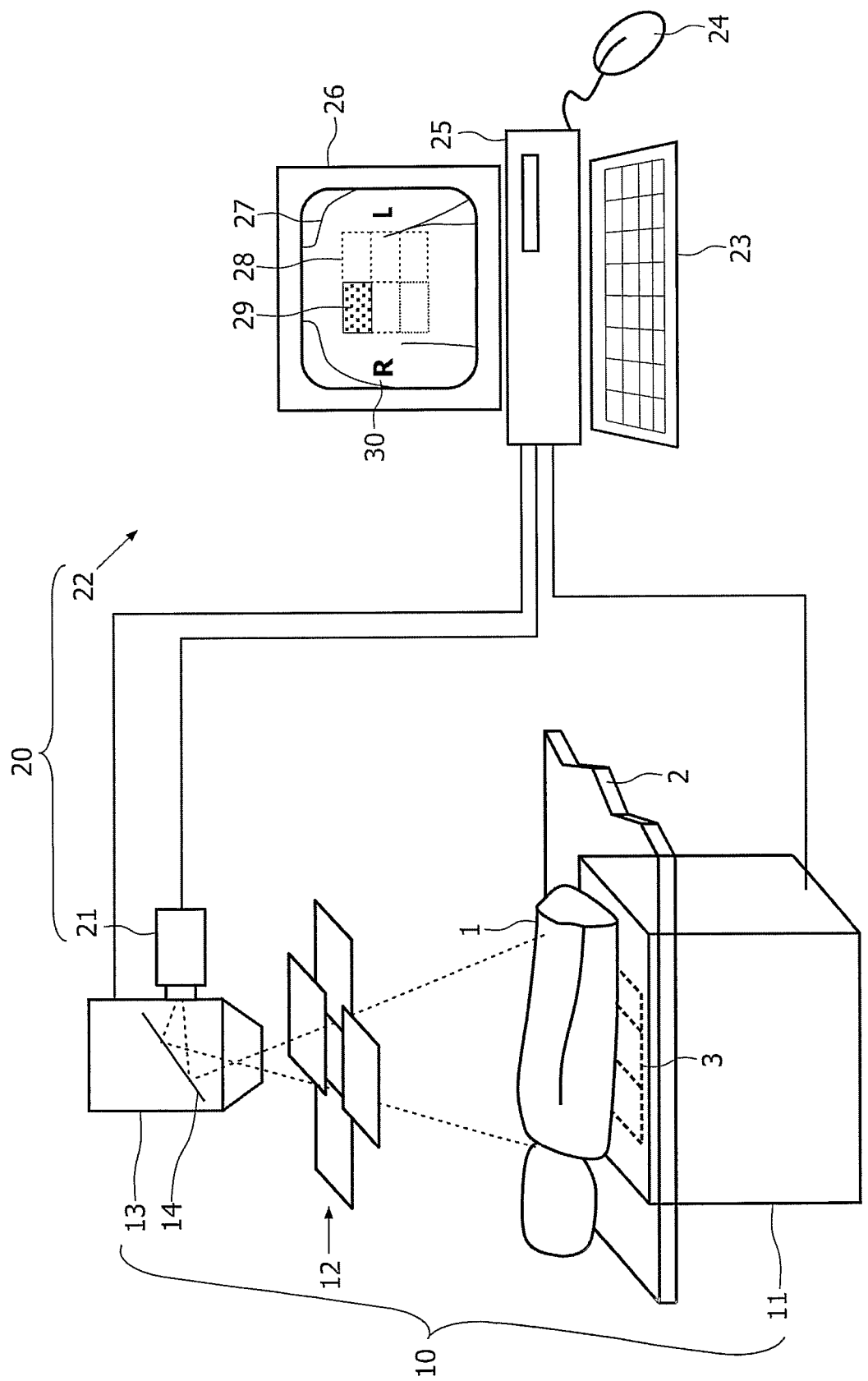

METHOD AND SYSTEM FOR THE PLANNING OF IMAGING PARAMETERS

The invention relates to an assistance system and a method for the planning of imaging parameters that are used by a main imaging system, particularly by an X-ray device.

When images of a patient are generated with a medical imaging device, many parameters have to be set in advance to guarantee an optimal image quality. During the generation of X-ray projections of a patient, for example, the shutter positions of a collimator have to be set in order to irradiate the correct region of interest. Moreover, many X-ray devices have dose-measuring-fields of different size and location which can selectively be activated to control the applied dose of an X-ray exposure in a closed loop. The aforementioned geometrical imaging parameters are nowadays selected manually, i.e. by the medical staff that for example adjusts the shutters of a collimator while observing light projected through the shutters onto the patient's body. Similarly, a patient is positioned on dose-measuring-fields that are indicated by markings on an X-ray detector, which typically is a difficult task because said markings are concealed by the patient's body.

This object is achieved by an assistance system according to claim 1, by a method according to claim 7, and by a record carrier according to claim 10. Preferred embodiments are disclosed in the dependent claims.

According to a first aspect, the invention comprises an assistance system for the planning of geometrical imaging parameters which are used for the imaging of an object with a main imaging system and which are in a broad sense related to the geometry of the imaging process. The "main imaging system" may for example be an X-ray device, a PET (Positron Emission Tomography) or SPECT (Single Photon Emission Computed Tomography) device, a Magnetic Resonance Imaging (MRI) device, or an ultrasound (US) device. The assistance system comprises the following components:

A camera for the generation of an optical image of the object that shall be imaged by the main imaging system, wherein the object is assumed to be (at least approximately) in the position it shall have during the intended exposure with the main imaging system.

An image processing system comprising a display unit, wherein said image processing system is coupled to the aforementioned camera and furthermore adapted to display on said display unit a geometrically registered overlay of an optical image of the object generated by said camera and of a graphical representation of imaging parameters. The "geometrical registration" means that the geometrical data which are encoded by the geometrical imaging parameters are displayed at the correct corresponding locations in the optical image. If the geometrical imaging parameters for example represent the shutter positions of a collimator, the corresponding irradiated area may be depicted geometrically correct on the optical image of the object.

The aforementioned assistance system has the advantage that it allows an observation and a selection of geometrical imaging parameters on a monitor with the help of a video image of the object. This is much easier and often also more accurate than the immediate setting of said parameters.

The values of the geometrical imaging parameters that are graphically represented in the overlay may be theoretically available and/or actually chosen values. Preferably, available and actually set values are displayed simultaneously but distinct, for instance in different colors. Thus for example all available dose-measuring-fields can be indicated on the overlay image in grey while the currently activated measuring fields are shown in color or otherwise highlighted.

As already mentioned, the geometrical imaging parameters which can be planned with the help of the assistance system may particularly relate to at least one dose-measuring-field that is used for the dose control of an X-ray imaging system. The imaging parameters may for example define the location and/or size of the activated dose-measuring-field. The indication of available and/or currently chosen dose-measuring-fields in an optical image of a patient allows an easy and accurate planning of said parameters. Moreover, the dose the patient is exposed to can be minimized because retakes of wrong exposures can be avoided.

According to another embodiment of the invention, the geometrical imaging parameters may relate to the setting of a collimator of an X-ray imaging system. In this case the irradiated region of interest may be chosen by the medical staff from a remote location, e.g. from a shielded control room.

The geometrical imaging parameters may furthermore relate to marks (symbols, indicators, signs, . . . ) that shall be permanently added to or imprinted on an image generated by the main imaging system. In X-ray imaging for example, markers of lead are often put on the detector in order to indicate the left/right projection of an organ on the resulting X-ray image. Such a positioning of real markers could be replaced by the use of virtual marks which can be set and manipulated on the optical image of a patient and later be transferred to the corresponding (digital) X-ray image.

In a further development of the assistance system, the image processing system comprises an input device like a touch screen, a keyboard or a mouse for the interactive setting of imaging parameters. Thus the values of the parameters may not only be indicated and verified on a display of the assistance system, but also actively manipulated.

The camera may in principle be arranged at any place from where it can generate the desired optical image of the object. According to a preferred embodiment, the camera is optically coupled (e.g. via a mirror) into the optical path of the main imaging system, thus seeing the object from exactly the same perspective.

The invention further relates to a method for the planning of geometrical imaging parameters that are used during the imaging of an object with a main imaging system, wherein said method comprises the following steps:

The generation of an optical image of the object.

The display of a geometrically registered overlay of said optical image and of a graphical representation of imaging parameters.

The method comprises in general form the steps that can be executed with an assistance system of the kind described above. Therefore, reference is made to the preceding description for more information on the details, advantages and improvements of that method.

According to a particular embodiment of the method, values for the geometrical imaging parameters are interactively chosen with the help of the displayed overlay and then applied by the main imaging system. In this case the use of the displayed overlay allows both a comfortable and accurate setting of the imaging parameters.

According to another embodiment of the method, the object and/or the main imaging system is repositioned according to the displayed overlay. This means that the relative position of the object and the imaging system is treated as a geometrical imaging parameter, too, which can be controlled and adjusted with the help of the optical image. Optionally an image processing software may be provided which recognizes the position of the object on the optical image and then automatically transfers the main imaging system into a position that correctly maps the region of interest.

Finally, the invention comprises a record carrier, for example a floppy disk, a hard disk, or a compact disc (CD), on which a computer program for the planning of geometrical imaging parameters that are used during the imaging of an object with a main imaging system is stored, wherein said program is adapted to execute a method of the aforementioned kind.

In the following the invention is described by way of example with the help of the accompanying single drawing, which schematically represents an X-ray device combined with an assistance system for the selection of geometrical imaging parameters according to the present invention.

The left part of the Figure shows a conventional X-ray system 10 comprising an X-ray source 13, a collimator 12 with four shutters, and an X-ray detector 11. A (transparent drawn) patient table 2 with a patient 1 lying on it is disposed between the X-ray source 13 and the detector 11. Thus X-ray projections of the chest of the patient 1 can be generated, wherein the exact location and size of the irradiated region of interest is determined by the position of the shutters in the collimator 12.

Within the X-ray device 10, the X-ray dose is controlled and limited by a dose measuring chamber (not shown) comprising several dose-measuring-fields of different size and position. The active measuring fields can be selected before an exposure depending on the region of interest to be X-rayed. To allow such a selection, the measuring fields are indicated by markings 3 on the surface of the X-ray detector 11. As the patient 1 has however a position very close to said surface of the detector 11, the markings are hardly visible and thus the correct selection of measuring fields and the correct positioning of the patient in relation to the markings is difficult. This often ends in wrong exposures with sub-optimal image quality which sometimes even have to be repeated, thus burdening the patient with additional dosage.

In order to improve the aforementioned situation, an assistance system 20 for the planning of geometrical imaging parameters is proposed. Said assistance system 20 comprises a video camera 21 (e.g. a CCD camera) which is adapted to generate a digital optical image of the patient 1 on the table 2. In the depicted embodiment said camera 21 is fixed to the collimator 12 at an angle of 90° with respect to the optical path of the X-ray system 10, wherein a mirror 14 (which is transparent for X-rays) deflects light rays coming in through the shutters of the collimator 12 towards the camera. Thus the camera 21 avoids errors due to a parallax that would arise with an arrangement of the camera parallel to the collimator/X-ray tube. The optical image of the camera 21 is transferred to the computer 25 (workstation) of an image processing system 22, wherein the computer is equipped with the conventional components like CPU, memory, I/O interfaces and the like together with appropriate software. The computer 25 is preferably also connected to the X-ray apparatus 10 in order to sense and/or set imaging parameters of the X-ray device 10 and for the processing of images generated by said device.

The main function of the computer 25 is the display of an image 27 of the patient 1 that was taken by the camera 21 on the monitor 26 together with an overlay 28 that represents certain geometrical imaging parameters. In the example depicted in the Figure, the overlay 28 represents the location of dose-measuring-fields with respect to the patient 1 and left/right markers 30. The measuring fields and the markers can be displayed at the correct position because the geometrical relation between the camera 21 and the X-ray device 10 is assumed to be known, thus allowing a geometrically correct registration of the camera image 27 with geometrical parameter values inherent to the X-ray device 10.

Furthermore, the computer 25 may not only display the available measuring fields 28, but also indicate the currently selected or activated measuring field(s) 29. This active measuring field 29 may for example be shown in a different color or highlighted. The user may then interactively change or choose the activated measuring field 29 via the keyboard 23 or the mouse 24. In a preferred embodiment, the monitor 26 is built as a touch screen on which the user can manipulate graphical objects by simply touching them with a finger (e.g. activate a measuring field 29).

Furthermore, the assistance system 20 can be used to set the position of virtual markers 30 which indicate the left and right side of the patient on the resulting X-ray image 27. The virtual markers 30 may for example be shifted on a touch screen with the fingers to a target location, from which they are transferred to the corresponding location on the digital X-ray image 27 that is generated by the detector 11.

Though not shown in the Figure, the assistance system 20 may also be used to monitor and/or set the shutter positions of the collimator 12. In this case, the currently chosen radiation field would be indicated on the optical image 27 of the patient 1. This enables a setting of correctly positioned shutters in a comfortable and accurate way that is new in this area (only for radiotherapy an overlay of the calculated radiation area to a CT image was described in JP 63294839 A2).

The invention has been described with reference to the preferred embodiments. Modifications and alterations may occur to others upon reading and understanding the preceding detailed description. It is intended that the invention be construed as including all such modifications and alterations insofar as they come within the scope of the appended claims or the equivalents thereof.

In summary, the system displayed in the Figure has the following advantages:
Faster operation as with normal systems by simplifying the workflow because the check of correct measuring-fields is much quicker.
Avoidance of wrong exposures because of wrong selected measuring-fields.
Avoidance of wrong exposures because of wrong positioning of measuring-fields in relation to the patients body.
Collimation from a remote control room without radiation.

Finally it is pointed out that in the present application the term "comprising" does not exclude other elements or steps, that "a" or "an" does not exclude a plurality, and that a single processor or other unit may fulfill the functions of several means. The invention resides in each and every novel characteristic feature and each and every combination of characteristic features. Moreover, reference signs in the claims shall not be construed as limiting their scope.

The invention claimed is:

1. An assistance system for the planning of geometrical imaging parameters that are used during the imaging of an object with a main imaging system, comprising:
   a camera for the generation of an optical image of the object;
   an image processing system with a display unit, wherein said image processing system is coupled to the camera and is adapted to display on the display unit a geometrically registered overlay of an optical image of the object and of a representation of geometrical imaging parameters.

2. The assistance system according to claim 1, wherein the main imaging system further comprises:
   an X-ray, PET, SPECT, MRI or ultrasound device.

3. The assistance system according to claim 1, wherein the representation of geometrical imaging parameters relates to the available and/or currently set values of geometrical imaging parameters.

4. The assistance system according to claim 1, wherein the geometrical imaging parameters are related to at least one of the following entities: a dose-measuring-field for the control of an X-ray imaging system, the setting of a collimator of an X-ray imaging system, and/or marks to be added to an image generated by the main imaging system.

5. The assistance system according to claim 1, wherein the image processing system comprises an input device for the interactive setting of imaging parameters.

6. The assistance system according to claim 1, wherein the camera is optically coupled into an optical path of the main imaging system.

7. A method for the planning of geometrical imaging parameters that are used during the imaging of an object with a main imaging system, comprising the following steps:
   generating an optical image of the object;
   generating a representation of geometrical imaging parameters;
   displaying a geometrically registered overlay of said optical image and the representation of geometrical imaging parameters.

8. The method according to claim 7, further including:
   interactively choosing values for the geometrical imaging parameters according to the displayed overlay; and
   overlaying the chosen geometrical imaging parameters to the main imaging system.

9. The method according to claim 7, further including:
   representing the object and/or the main imaging system according to the displayed overlay.

10. A record carrier on which a computer program for the planning of geometrical imaging parameters that are used during the imaging of an object with a main imaging system is stored, said program being configured to execute a method according to claim 7.

11. The method according to claim 7, wherein the geometrical imaging parameters include at least one dose measuring field.

12. The method according to claim 11, wherein the geometrical imaging parameters further include virtual marks that indicate left and right.

13. An assistance system for planning dose measuring fields comprising:
   an image processing computer programmed to perform the method according to claim 11.

14. The method according to claim 7, wherein the display includes a touch screen and the geometrical imaging parameters include a plurality of dose measuring fields, the method further including:
   touching one or more of the dose measuring fields displayed on the touch screen to select one or more dose measuring fields to be activated.

15. The method according to claim 14, further including:
   indicating the one or more selected dose measuring fields on the display.

16. An assistance system for planning dose measuring fields that are used during the imaging of a subject with a main imaging system, the assistance system comprising:
   a video camera which generates an optical image of the subject;
   an imaging processing system which geometrically registers a plurality of dose measuring fields with the optical image; and
   a monitor which displays an image of the geometrically registered dose measuring fields overlaid with the optical image.

17. The assistance system according to claim 16, wherein the monitor includes a touch screen, such that dose measuring fields in the displayed image are touched to be selected or deselected.

18. The assistance system according to claim 17, wherein each selected dose measuring field is indicated on the displayed image.

* * * * *